United States Patent [19]

Haug et al.

[11] 4,130,564

[45] Dec. 19, 1978

[54] PROCESS FOR THE MANUFACTURE OF MALEIMIDES

[75] Inventors: Theobald Haug, Frenkendorf; Jürg Kiefer, Reinach; Alfred Renner, Münchenstein, all of Switzerland

[73] Assignee: Ciba-Geigy Corporation, Ardsley, N.Y.

[21] Appl. No.: 782,681

[22] Filed: Mar. 30, 1977

[30] Foreign Application Priority Data

Apr. 9, 1976 [CH] Switzerland .......................... 4535/76

[51] Int. Cl.$^2$ .................. C07D 207/00; C07D 207/02
[52] U.S. Cl. .......................... 260/326.26; 260/326.41; 260/326.5 FM; 546/281; 546/308; 546/309
[58] Field of Search ................ 260/326.5 FM, 326.26, 260/295 D, 326.41

[56] References Cited

U.S. PATENT DOCUMENTS

| | | | |
|---|---|---|---|
| 3,839,358 | 10/1974 | Bargain | 260/326.26 |
| 3,868,351 | 2/1975 | Hand et al. | 260/78 UA |
| 3,960,887 | 6/1976 | Renard | 260/326.5 FM |
| 3,996,203 | 12/1976 | Hand et al. | 260/78 UA |

*Primary Examiner*—Jose Tovar
*Attorney, Agent, or Firm*—Luther A. R. Hall

[57] ABSTRACT

The invention relates to the improvement of the conventional processes for manufacturing monomaleimides and polymaleimides, in which it is known to cyclodehydrate corresponding monomaleamic or polymaleamic acids in the presence of acetic anhydride and tertiary amines. According to the invention, the tertiary amines are used only in very small amounts (0.1 to 0.5 mole per mole of maleamic acid group) and the dehydration is carried out at temperatures between 10° and 50° C. The end products are obtained in purer form and greater yield than in conventional processes.

11 Claims, No Drawings

PROCESS FOR THE MANUFACTURE OF MALEIMIDES

The invention relates to a process for the manufacture of monomaleimides and polymaleimides, which have lately become of considerable importance as starting materials for obtaining heat-resistant polymers.

Numerous methods of manufacturing such maleimides are already known. These methods comprise converting the corresponding monomaleamic or polymaleamic acids into the end product by a cyclodehydration reaction at elevated temperature. In this connection attention is drawn for example to the following patent specifications: U.S. Pat. Nos. 3,127,414 and 3,018,290, British Pat. Nos. 1,137,592 and 1,175,488, and DT-OS 2,040,094.

According to the methods described in U.S. Pat. No. 3,127,414 and British Pat. No. 1,137,592, the process is carried out in the presence of alkali salts of organic acids and polar organic solvents. The disadvantage of this method is that relatively large amounts of these expensive solvents are consumed and that, on account of the water which is added, they cannot be recovered or can only be recovered by using complicated apparatus. A further disadvantage is the large amount of anhydrous sodium acetate and the large amount of water (up to a 180-fold excess) which is used to precipitate the reaction product. This substantial excess of water also causes the by-products of the reaction to precipitate together with the maleimide, which consequently contains a high degree of impurities.

The large amount of water causes a low reactor yield. It is a prominent feature of both processes that in the Examples the reaction is carried out without exception at elevated temperatures. In column 1, lines 51 and 52 of the U.S. patent, it is furthermore emphasised that the reaction proceeds too slowly when applying temperatures below 45° C. and that for practical purposes it is not possible to carry out a process at such temperatures.

Temperatures of approx. 60° C. are also used throughout in the process of British Pat. No. 1,175,488, which is similar to the two processes discussed above. As in the processes already discussed, the use of such temperatures also causes a relatively large formation of by-products. Since in this process large amounts of expensive aprotic solvents are required, it also has the same disadvantage that a difficult reprocessing of these solvents is necessary.

DT-OS No. 2,040,094 describes a process in which the cyclisation reaction to give the maleimide is also carried out in the presence of large amounts of an organic diluent, in the presence of an tertiary amine and of a nickel salt. This process yields a relatively pure imide, but in order to isolate it a large amount of water is added, which in turn results in an uneconomic reactor yield. According to Example 1 of this German Offenlegungsschrift, the manufacture of only 310 kg of bisimide results in approx. 2.5 tons of strongly aqueous solvent, whilst the toxicity of the nickel salt can give rise to difficulties in purifying the effluent. Another disadvantage of this process is that a large number of by-products form, for example adducts of acetic acid with the double bond of the maleimide. This formation of by-products is probably attributable to the high cyclisation temperature (50° to 80° C.) which is necessary, however, for a rapid cyclisation.

According to the process described in U.S. Pat. No. 3,018,290 and in J. Org. Chem. 26, 10–15 (1961) and in J. Org. Chem. 36, 821–823 (1971), acetic anhydride and triethylamine are also used, inter alia, in the cyclodehydration. Triethylamine is required in an amount of at least 2 moles per mole of maleic acid group. The reason given for this disadvantageously large amount of triethylamine in J. Org. Chem. 36, 821 (1971) is that too small amounts result in a reduced product yield. The acid-catalysed hydrolysis of the isoimide initially formed is cited as the cause of this. In addition, the excess amount of tertiary amine is allegedly required in order to form chiefly the imide and little isoimide.

Apart from the disadvantage of having to use a relatively large amount of tertiary amine, this last described prior art process has the following additional three drawbacks. Since the process must be carried out in the presence of substantial amounts of organic solvents (their weight is at least 50% of the weight of the starting materials), the complicated reprocessing already referred to results again.

Furthermore, the yields are fairly low: in the Examples they vary between 54 and 61% of theory. Finally, the low melting point indicates that the end products contain a high degree of impurities.

The invention has for its object to provide a process which gives purer end products in better yield than the processes of the prior art. The reactor yield will be sufficiently large. The use of organic solvents will be superfluous in such a process or will be limited to minimum amounts.

Accordingly, the invention provides a process for the manufacture of maleimides of the general formula I

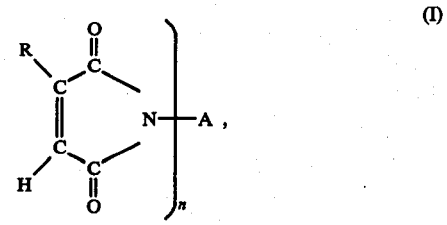

wherein n is one of the integers 1, 2 or 3, and R represents a hydrogen atom or a linear or branched alkyl group having a total of 1 to 4 carbon atoms, preferably a hydrogen atom, and A represents a n-valent branched or unbranched aliphatic radical having a total of 2 to 30 carbon atoms, a cycloaliphatic, aromatic, heterocyclic or araliphatic radical, by cyclodehydrating corresponding monomaleimic or polymaleamic acids of the general formula II

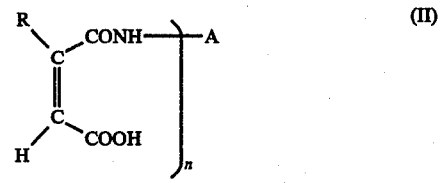

in the presence of low molecular, dehydrating carboxylic anhydrides and tertiary amines, and in the presence or absence of organic solvents, which process comprises the use of tertiary amines in an amount of 0.1 to 0.5 mole per mole of maleamic acid group and carrying out the cyclodehydration at temperatures between 10° and 50° C., preferably between 20° and 40° C.

As polymaleamic acids of the formula II it is possible to use in particular substances of the formula III

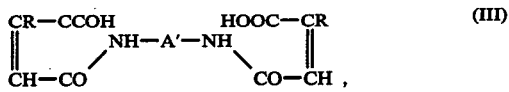

wherein A' represents a branched or unbranched aliphatic radical having a total of 2 to 12 carbon atoms, a cycloaliphatic, aromatic, heterocyclic or araliphatic radical.

A cycloaliphatic radical is for example the cyclohexylene radical, an aromatic radical is the phenylene radical, and a heterocyclic radical is the radical of the formula

The symbol A' in formula III can also consist of several phenylene or cyclohexylene radicals which are linked to each other by a simple valence bond or by an alkylene group of 1 to 3 carbons or a group

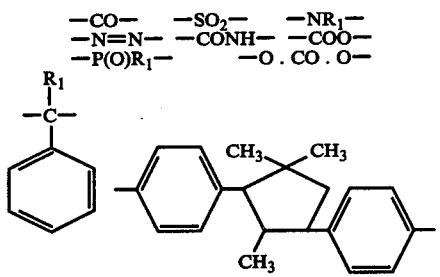

wherein $R_1$ represents a hydrogen atom or an alkyl radical of 1 to 4 carbon atoms or a phenyl radical.

The different phenylene or cyclohexylene radicals can furthermore carry substituents which do not adversely affect the subsequent reactions, for example groups such as —CH₃, —C₂H₅, —C(CH₃)₃, —OH, OR', —Cl, —Br, —NO₂, —COOR', —CONR'. R' represents herein a linear or branched alkyl radical of 1 to 6 carbon atoms.

A preferred embodiment of the invention comprises the use of those polymaleamic acids of the formula III which contain several aromatic radicals, in which a radical of the formula

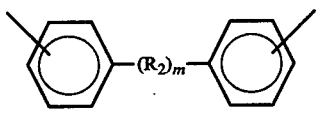

wherein $R_2$ represents one of the radicals —CH₂—,

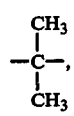

—SO₂—, —SO—, —S—, —CO— and —O—, and m is 0 or 1, is A' in formula III.

4,4'-Diphenylmethane-bis-maleamic acid is to be particularly mentioned as an example of such starting products for the process.

Further examples of monomaleamic and polymaleamic acids of the formula III are the following substances:

N-phenyl-maleamic acid
N-tolyl-maleamic acid
o-hydroxyl-N-phenyl-maleamic acid
m-hydroxyl-N-phenyl-maleamic acid
p-hydroxy-N-phenyl-maleamic acid
4-hydroxy-3,5-di-tert.-butyl-N-phenyl-maleamic acid
4-carboxy-N-phenyl-maleamic acid
N,N'-ethylene-bis-maleamic acid
N,N'-hexamethylene-bis-maleamic acid
N,N'-m-phenylene-bis-maleamic acid
N,N'-p-phenylene-bis-maleamic acid
N,N'-4,4'-diphenyl ether-bis-maleamic acid
N,N'-4,4'-diphenylsulphone-bis-maleamic acid
N,N'-4,4'-dicyclohexylmethane-bis-maleamic acid
N,N-4,4'-diphenylsulphide-bis-maleamic acid
N,N'-m-xylylene-bis-maleamic acid
N,N'-4,4'-(1,1-diphenylcyclohexane)-bis-maleamic acid,
N,N'-1,4-cyclohexylene-bis-maleamic acid
N,N'-4,4'-diphenylene-bis-maleamic acid
N,N'-1,5-naphthylene-bis-maleamic acid
N,N'-4,4'-dicyclohexylpropane-bis-maleamic acid
N,N'-4,4'-benzophenone-bis-maleamic acid
N,N'-4,4'-phenylbenzoate-bis-maleamic acid
N,N'-4,4'-benzanilide-bis-maleamic acid
1,4-tetramethylene glycol-bis-(p-maleamic acid)-benzoate
1,10-decamethylene glycol-bis-(p-maleamic acid)-benzoate
ethylene glycol-bis-(o-maleamic acid)-benzoate
N,N'-3,3'-dichloro-4,4'-diphenylmethane-bis-maleamic acid
N,N'-2,5-dichloro-p-phenylene-bis-maleamic acid
N,N'-4,4'-diphenylmethane-bis-citraconamic acid
1,1,3-trimethyl-3-p-aminophenyl-5(6)-amino-indane-bis-maleamic acid
N,N',N''-4,4',4''-triphenylphosphate-tris-maleamic acid.

The maleamic acids used in the process of the present invention can be obtained by the methods known for this purpose. Attention may be drawn in this respect to "Maleic Anhydride Derivatives" by L. A. Flett and W. H. Gardner.

Examples of suitable tertiary amines are in particular trialkylamines and the N,N-dialkylbenzylamines in which the alkyl moieties contain from 1 to 12 carbon atoms. Triethylamine and N,N-dimethylbenzylamine are preferably used.

As low molecular, dehydrating carboxylic anhydride it is advantageous to use acetic anhydride in an amount of at least 1.2 moles per mole of maleamic acid group. In general, larger amounts in the order of 1.5 to 2 moles per mole of maleamic acid group are used.

The reaction of the present invention is preferably carried out in the absence of an organic solvent, whilst the reactants are not to be understood as solvents. However, the reaction can also be carried out in the presence of an organic solvent whose task it chiefly is to dilute the suspensions obtained in the process in such a way that they can be easily handled. Suitable examples of such diluents are aprotic substances, such as dimethyl formamide or N-methylpyrrolidone, and also short-chain aliphatic ketones or esters, for example acetone, methyl ethyl ketone or ethyl acetate. They are preferably added in an amount between 5 and 30% of the amount of the other liquid reactants.

In practice, the process of the invention is carried out by adding the maleamic acid of the general formula II, with stirring at room temperature or at slightly elevated temperature, to a mixture of the anhydride, the tertiary amine and —if one is used— the diluent. The temperature is so regulated that it does not exceed 50° C. and preferably does not exceed 40° C. When the addition is complete, the reaction is brought to completion at this temperature, for which as a rule 1 to 4 hours are required. The imide is frequently obtained as a crystalline substance. The crystallisation and purity can be improved by inoculating the reaction product with pure imide. The yield can be increased by adding a precipitant, for example water, but low molecular alcohols, such as methanol or isopropanol, or carboxylates (for example ethyl acetate) as well as aliphatic carboxylic acids (for example acetic acid) can also be used. The amount of precipitant should be as small as possible in order to obtain maximum purity, product and reactor yield. In general, at most an amount of precipitant is used which is equal to the sum of the volumes of the other liquid reactants, but preferably an amount which is 0.2 to 0.5 times the sum of the other liquid reactants.

As has been mentioned already, particularly pure end products are obtained in high yield when carrying out the process of the invention. This is due in particular to maintaining low temperatures and to the use of small amounts of tertiary amines. The process of the invention is preferably carried out in the absence of metal compounds. However, in many cases the process can be carried out also in the presence of additional small amounts of metal compounds, in particular of metal salts of organic acids, in order to shorten the reaction time.

EXAMPLE 1

A reaction vessel is charged with 153 g of acetic anhydride, 50 g of triethylamine and 50 ml of dimethyl formamide. With stirring, 197 g of N,N'-4,4'-diamino-diphenylmethane-bis-maleamic acid are added in small amounts. As soon as this substance has dissolved, the contents of the flask are heated for 3 hours to 37°–40° C. After cooling to approx. 10° C., the batch is filtered to yield 157 g (88% of theory) of a yellow substance which the analytical data show to be N,N'-4,4'-diaminodiphenylmethane-bis-maleimide with a melting point of 151°–153° C.

EXAMPLE 2

The procedure of Example 1 is followed, except that 2 g of calcium-bis-O-ethyl-4-hydroxy-3,5-di-tert.-butyl-benzyl)-phosphonate are added to the reaction solution before adding the maleamic acid. After the acid has dissolved, the contents of the reaction flask are heated with stirring to a maximum temperature of 40° C. The bis-maleimide is isolated as described in Example 1 in a yield of 162 g (90.5% of theory) with a melting point of 153°–155° C.

EXAMPLE 3

The procedure of Example 1 is followed, except that the reaction is carried out in the absence of dimethyl formamide and that 2 g of cobalt naphthenate are added to the reaction solution before adding the maleamic acid. After the acid has dissolved, the batch is heated with stirring for 2 hours to a maximum temperature of 40° C. The bis-maleamide is isolated as described in Example 1 in a yield of 166 g (93% of theory) with a melting point of 152°–154° C.

EXAMPLE 4

A reaction vessel is charged with 153 g of acetic anhydride, 35 g of triethylamine and 2 g of cobalt naphthenate. With stirring, 197 g of N,N'-4,4'-diamino-diphenylmethane-bis-maleamic acid are added in small amounts. The reaction mixture is thereafter heated for 2 hours to a maximum temperature of 40° C. and subsequently 150 ml of water are added. The suspension is kept for a further 1½ hours at 0°–5° C. and then filtered. The residue is washed with water and dried to yield 163 g (91% of theory) of N,N-4,4'-diamino-diphenylmethane-bis-maleimide with a melting point of 151°–153° C.

EXAMPLE 5

A reaction vessel is charged with 140 ml of acetic anhydride and 84 ml of tributylamine. With stirring, 191 g of N-phenylmaleamic acid are added in small amounts. After all the ingredients have dissolved, the reaction mixture is kept for 6 hours at 35°–40° C. After cooling to 15° C., 150 ml of water are added and the precipitated product is filtered off after 1 hour to yield 140 g (81% of theory) of a light yellow crystalline substance which melts at 84°–86° C. and which the analytical data show to be N-phenyl-maleimide.

EXAMPLE 6

159 g of N,N'-2,4'-toluylene-bis-maleamic acid are added in small amounts to 140 ml of acetic anhydride and 50 ml of triethylamine. After all the ingredients have dissolved, the reaction mixture is kept for 5 hours at 38°–42° C. After cooling to 10° C., 150 ml of water are added dropwise and the batch is filtered to yield 124 g of a dark yellow crystalline substance (88% of theory) which has a melting point of 168.5°–170° C. and which the analytical data show to be N,N'-2,4'-toluylene-bis-maleimide.

EXAMPLE 7

With stirring, 152 g of 1,10-decamethylene glycol-bis-(p-maleamic acid)-benzoate are added in small amounts to 76.5 g of acetic anhydride and 33.75 g of N,N-dimethylbenzylamine. After all the ingredients have dissolved, the reaction mixture is kept for 2½ hours at 30°–36° C. and then cooled to 10° C. Then 75 ml of water are added dropwise and the precipitated product is filtered off to yield 124 g (86.74% of theory) of a light beige-coloured crystalline powder which the analytical data show to be 1,10-decamethylene glycol-bis-(p-maleimide)-benzoate with a melting point of 106°–110° C.

EXAMPLE 8

With stirring, 39.6 g of N,N'-4,4'-diphenyl ether-bis-maleamic acid are added in small amounts to 30.6 g of acetic anhydride and 10.1 g of triethylamine. After all the ingredients have dissolved, the reaction mixture is kept for 5 hours at 38°–42° C., then cooled to approx. 10° C. Then 30 ml of water are added dropwise and the precipitated product is filtered off to yield 33.80 g of a yellowish brown crystalline powder (93.8% of theory) which the analytical data show to be N,N'-4,4'-diphenyl ether-bis-maleimide with a melting point of 175°–177° C.

EXAMPLE 9

With stirring, 39.6 g of N,N'-4,4'-diphenylsulphone-bis-maleimic acid are added by small amounts to 30.6 ml of acetic anhydride and 10.1 g of triethylamine. After all the ingredients have dissolved, the reaction mixture is kept for 5 hours at 40°–45° C., then cooled to approx. 10° C. Then 30 ml of water are added and the precipitated product is filtered off to yield 38.60 g (94.6% of theory) of a pink crystalline substance which the analytical data show to be N,N'-4,4'-diphenylsulphone-bis-maleimide with a melting point of over 30° C.

EXAMPLE 10

With stirring, 219.4 g of N,N',N''-4,4',4''-triphenyl-phosphate-tris-maleamic acid. After all the ingredients have dissolved, the reaction mixture is kept for 4 hours at 30°–40° C., then cooled to 10° C. After the dropwise addition of a mixture of 75 ml of water and 50 ml of methanol, the precipitated product is filtered off to yield 132 g (71.35% of theory) of a light brown crystalline powder which the analytical data show to be N,N',N''-triphenylphosphate-tris-maleimide with a melting point of 175°–180° C.

EXAMPLE 11

With stirring, 211 g of a mixture of 7% of N,N'-4,4'-diphenylmethane-bis-maleamic acid, 49% of 3-methyl-N,N-4',4'-diphenylmethane-bis-maleamic acid and 44% of 3,3'-diethyl-N,N-4,4'-diphenylmethane-bis-maleamic acid are added in small amounts to 140 ml of acetic anhydride and 50 ml of triethylamine. After all the ingredients have dissolved, the reaction mixture is kept for 4 hours at 35°–40° C., then cooled to 10° C. Then 150 ml of water are added dropwise and the precipitated product is filtered off to yield 186 g (96% of theory) of crystalline substance which the analytical data show to be the bis-maleimide with a melting point of 142°–152° C.

EXAMPLE 12

With stirring, 42.2 g of N,N'-4,4'-diphenylmethane-bis-methylmaleamic acid are added in small amounts to 30.6 g of acetic anhydride and 10.1 g of triethylamine. After all the ingredients have dissolved, the reaction mixture is stirred for 2 hours at 30°–35° C., then cooled to 10° C. A mixture of 15 ml of water and 15 ml of methanol is then added and the precipitated product is filtered off to yield 32.4 g (83.9% of theory) of a yellow crystalline substance which the analytical data show to be N,N'-4,4'-diphenylmethane-bis-methylmaleimide with a melting point of 126.5°–128° C.

EXAMPLE 13

31.2 g of N,N'-hexamethylene-bis-maleamic acid are added in small amounts to 30.6 g of acetic anhydride and 10.1 g of triethylamine. When the addition is complete, the reaction mixture is kept for 6 hours at 38°–40° C., then cooled to 10° C. Then 30 ml of water are added dropwise and the precipitated product is filtered off to yield 18 g (65% of theory) of a light beige-coloured crystalline substance which the analytical data show to be N,N'-hexamethylene-bis-maleimide with a melting point of 134°–136.5° C.

Comparison Example A

The procedure of Example 1 is followed, except that the reaction mixture is heated for 3 hours to 60° C. instead of only to 40° C. After working up the reaction mixture exactly as described in Example 1, an initially resinous brown product is obtained, which after standing for a prolonged period of time decomposes into a brown powder. Filtration yields solely 106 g (59% of theory) of a brown powder with a melting point of 105°–127° C. This crude product contains only 40% of pure bis-maleimide.

Comparison Example B 8.9 g (0.225 mole) of chromatographed N,N'-4,4'-diphenyl-methane-bis-maleimide (m.p. 163°–164° C., the content of pure bis-imide and the content of olefinic double bonds being 99% of theory in each case), 7.6 g (0.075 mole) of acetic anhydride, 3 g (0.025 mole) of acetic acid and 0.8 g of triethylamine are well mixed and the mixture is heated with stirring for 2 hours to 40° C. With vigorous stirring, the suspension is thereafter poured into 120 ml of ice-water, by means of which, after washing with water and drying, 8.8 g of a yellow crystalline powder with a melting point of 160°–162° C. and containing 97% of pure bis-imide and 98% of theory of olefinic double bonds are isolated.

Comparison Example C

The procedure of Comparison Example B is followed with the sole exception that 2.4 g (0.024 mole) of triethylamine are used instead of 0.8 g (0.008 mole). The yield consists of 8.7 g of beige-coloured crystals with a melting point of 155°–158° C. and containing 93% of pure bis-imide and 95% of theory of olefinic double bonds.

Comments on Example 1 and Comparison Example A

A comparison between Example 1 and Comparison Example A, in each of which the same amount of amine (0.5 mole per mole of maleamic acid group) is used, shows particularly the advance in the art in which the inventive feature of applying reaction temperatures between 10° and 50° C. results. In Example 1, the yield and purity of the end product are substantially better.

In Example 1, the cyclisation is carried out at a maximum temperature of 40° C., the yield is 88%, the content of olefinic double bonds is 94% of theory. In Comparison Example A on the other hand, in which the cyclisation is carried out at 60° C., the yield is only 59% and the content of olefinic double bonds is only 44% of theory. The thin-layer chromatograms of Example 1 and Comparison Example A show unequivocally that, in this latter Example, substantially more acetic acid/bis-maleimic adduct has been formed.

Discussion of Comparison Examples B and C

Both these Examples show the advantage of using small, less than equivalent amounts of tertiary amine. In these experiments, pure chromatographed N,N'-4,4'-diphenylmethane-bis-maleimide, glacial acetic acid, anhydride and triethylamine are heated, with stirring, for 2 hours at 40° C. The amount of glacial acetic acid corresponds to the amount which forms from acetic anhydride when completely cyclising the maleamic acid groups to the imide groups. Comparison Examples B and C differ in the amount of triethylamine: C contains 3 times as much as B. After heating for 2 hours, water is added, thus causing all solid reactants to precipitate. The powdery solid was analysed. The following table shows that in Example B, in which less triethylamine is present, the bis-maleimide is scarcely changed chemically in contradistinction to Example C, in which the 3-fold amount of amine effects a marked change of the maleimide.

|  | bis-maleimide used | product of comparison Example B | product of comparison Example C |
|---|---|---|---|
| melting point | 163-164° C | 160-162° C | 155-158° C |
| content of pure maleimide in gel chromatography | 99 | 97 | 93 |
| content of olefinic double bonds | 99% | 98% | 95% |

We claim:

1. In a process for manufacture of maleimides of the formula I

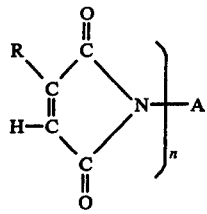

wherein n is one of the integers 1, 2 or 3, R represents hydrogen or a linear or branched alkyl having 1 to 4 carbon atoms, and where n is 1, A represents phenyl, tolyl, hydroxyphenyl, carboxyphenyl or 4-hydroxy-3,5-di-tert-butylphenyl; where n is 2, A represents alkylene of 2 to 12 carbon atoms, cyclohexylene, phenylene, naphthylene, pyridylene, xylylene or a plurality of phenylene or cyclohexylene radicals linked by a simple valence bond or by an atom or group which is inert under reaction conditions; or where n is 3, A represents

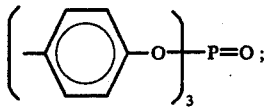

by cyclodehydrating the corresponding maleamic acid of the general formula II

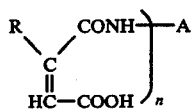

in the presence of a low molecular weight, dehydrating carboxylic acid anhydride and a tertiary amine in an amount of 0.1 to 0.5 mole of amine per mole of maleamic acid group, and in the presence or absence of an organic solvent, the improvement which comprises carrying out the cyclodehydration at a temperature between 10° C. and 50° C.

2. A process according to claim 1 where R is hydrogen.

3. A process according to claim 1 where the reaction is carried out between 20° C. and 40° C.

4. A process according to claim 1, wherein a trialkylamine or a N,N-dialkylbenzylamine each containing 1 to 12 carbon atoms in the individual alkyl moieties is used as tertiary amine.

5. A process according to claim 4, wherein triethylamine is used as tertiary amine.

6. A process according to claim 1, wherein the cyclodehydration is carried out in the absence of organic solvents.

7. A process according to claim 1, wherein the cyclodehydration is carried out in the presence of an organic solvent in an amount of 5 to 30% by weight, referred to the other liquid reactants.

8. A process according to claim 1 wherein a polymaleamic acid of the formula III

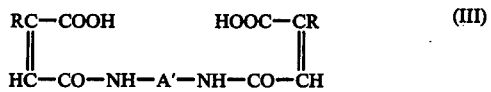

represents the polymaleamic acid of formula II where n is 2, in which R is hydrogen or alkyl of 1 to 4 carbon atoms and A' is alkylene of 2 to 12 carbon atoms, cyclohexylene, phenylene, naphthylene, pyridylene, xylylene or a plurality of phenylene or cyclohexylene radicals linked to one another by a simple valence bond or by alkylene of 1 to 3 carbon atoms, —CO— —SO$_2$—, —SO—, —S—, —O—, —NR$_1$—, —N=N—, —CONH—, —COO—, —P(O)R$_1$—, —OCOO—,

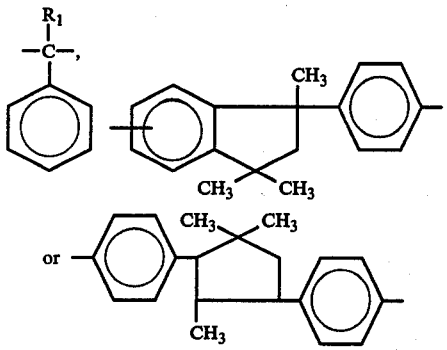

where R$_1$ is hydrogen, alkyl of 1 to 4 carbon atoms or phenyl.

9. A process according to claim 8 wherein R is hydrogen.

10. A process according to claim 8, wherein a polymaleamic acid of the formula III is used, in which A' represents a radical of the formula

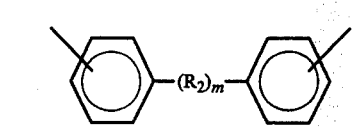

wherein R$_2$ represents one of the radicals —CH$_2$—,

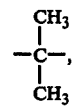

—SO$_2$—, —SO—, —S—, —CO— and —O—, and m is 0 or 1.

11. A process according to claim 10, wherein 4,4'-diphenylmethane-bis-maleamic acid is used as polymaleamic acid of the formula III.

* * * * *